(12) United States Patent
Szopinski et al.

(10) Patent No.: US 10,617,515 B2
(45) Date of Patent: Apr. 14, 2020

(54) SELF-EXPANDING VASCULAR PROSTHESIS

(71) Applicant: JOTEC GmbH, Hechingen (DE)

(72) Inventors: Piotr Szopinski, Warsaw (PL);
Christian Woerne, Ostfildern (DE);
Michael Walther, Lentfoehrden (DE)

(73) Assignee: JOTEC GMBH, Hechingen (DE)

( * ) Notice: Subject to any disclaimer, the term of this patent is extended or adjusted under 35 U.S.C. 154(b) by 27 days.

(21) Appl. No.: 16/020,904

(22) Filed: Jun. 27, 2018

(65) Prior Publication Data
US 2018/0303598 A1 Oct. 25, 2018

Related U.S. Application Data

(63) Continuation of application No. PCT/EP2016/082798, filed on Dec. 29, 2016.

(30) Foreign Application Priority Data

Dec. 30, 2015 (DE) .................. 10 2015 123 000

(51) Int. Cl.
A61F 2/07 (2013.01)
A61F 2/89 (2013.01)
A61F 2/915 (2013.01)
A61F 2/06 (2013.01)
A61F 2/856 (2013.01)

(52) U.S. Cl.
CPC .................. A61F 2/07 (2013.01); A61F 2/89 (2013.01); A61F 2/915 (2013.01); A61F 2/856 (2013.01); A61F 2002/061 (2013.01); A61F 2002/075 (2013.01); A61F 2002/91508 (2013.01); A61F 2250/0037 (2013.01); A61F 2250/0039 (2013.01)

(58) Field of Classification Search
CPC ...... A61F 2/07; A61F 2/82; A61F 2/89; A61F 2/91; A61F 2/954
See application file for complete search history.

(56) References Cited

U.S. PATENT DOCUMENTS

| | | |
|---|---|---|
| 2006/0095118 A1 | 5/2006 | Hartley |
| 2006/0195177 A1 | 8/2006 | Kaufmann et al. |
| 2009/0319022 A1 | 12/2009 | Hartley et al. |

FOREIGN PATENT DOCUMENTS

| | | |
|---|---|---|
| DE | 10337739 A1 | 3/2005 |
| DE | 102012103986 A1 | 11/2013 |

(Continued)

OTHER PUBLICATIONS

European Patent Office, International Search Report for International Application No. PCT/EP2016/082798, dated Mar. 10, 2017.

(Continued)

Primary Examiner — Jason-Dennis N Stewart
(74) Attorney, Agent, or Firm — Rimon, P.C.

(57) ABSTRACT

The present invention relates to a self-expanding vascular prosthesis for implantation in a blood vessel of a patient, comprising a hollow-cylindrical base body, a vascular prosthetic trunk having a first and a second opening, and at least two vascular prosthesis side branches which are outgoing from the vascular prosthetic trunk and are formed integrally with the vascular prosthetic trunk. The vascular prosthetic trunk has sections which comprise a tapered peripheral part, in which the vascular prosthesis side branches are mounted.

16 Claims, 2 Drawing Sheets

(56) References Cited

FOREIGN PATENT DOCUMENTS

| | | |
|---|---|---|
| EP | 2777610 A2 | 9/2014 |
| WO | 2010/024879 A1 | 3/2010 |
| WO | 2011/047004 A1 | 4/2011 |
| WO | 2013/167491 A1 | 11/2013 |
| WO | 2015/061669 A1 | 4/2015 |
| WO | 2015/109375 A1 | 7/2015 |

OTHER PUBLICATIONS

The International Bureau of WIPO, International Preliminary Report on Patentability and Written Opinion for International Application No. PCT/EP2016/082798, dated Jul. 3, 2018, 7 pages.

SELF-EXPANDING VASCULAR PROSTHESIS

CROSS-REFERENCES TO RELATED APPLICATIONS

This application is a continuation of international patent application PCT/EP2016/082798, filed on Dec. 29, 2016, designating the U.S., which international patent application has been published in German language and claims priority from German patent application DE 10 2015 123 000.3, filed on Dec. 30, 2015. The entire contents of these priority applications are incorporated herein by reference.

BACKGROUND OF THE INVENTION

The present invention relates to a self-expanding vascular prosthesis for implantation in a blood vessel of a patient, with a vascular prosthesis trunk having a hollow-cylindrical main body and also a first and a second opening, and with at least two vascular prosthesis side branches branching off from the vascular prosthesis trunk.

It is generally known for intraluminal vascular prostheses or implants, also referred to as endovascular stents or stent grafts, to be used for treating weakened, damaged or torn vessels or aneurysms. For this purpose, a vascular implant or stent graft is released at the diseased or damaged site of the vessel and restores the functionality of the original vessel or supports the still existing integrity of the vessel.

An aneurysm is understood here as a widening or bulging of an arterial blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding. The cause of a thoracic and thoraco-abdominal aortic aneurysm may be arteriosclerosis, high blood pressure and inflammation processes of the vessel wall. Injuries of the thorax due to serious accidents may also lead to acute or chronic aortic aneurysm.

The self-expanding vascular prostheses used for the treatment of aneurysms generally consist of a hollow-cylindrical metal frame or framework, of which the surface is covered by a textile or polymer film, such that a hollow-cylindrical body is obtained. For implantation, the vascular implant is radially compressed, such that its cross-sectional area is greatly reduced. With the aid of an insertion system, the vascular implant is then brought into the region of the aneurysm, where it is released. By virtue of the resilience of the metal frame or framework, the vascular implant expands again to its original shape and in so doing stretches its surface, which lodges inside the blood vessel proximally and distally in relation to the aneurysm. In this way, the blood now flows through the vascular implant, and further loading of the bulge is prevented.

The metal frame of such vascular implants generally consists, for example, of a wire mesh or of so-called stent springs, which are arranged one behind the other, extend in a meandering formation and, if appropriate, are connected to one another by connecting struts made of wire, or which are merely connected to one another via the material of the implant. The wire mesh or the stent springs are usually made of a shape-memory material, generally of Nitinol, as a result of which, after insertion into a vessel for release, the stent springs return to the expanded state and thus "open up" the vascular implant.

Aneurysms often occur in the region of the abdominal aorta (Aorta abdominalis) or thoracic aorta (Aorta thoracica), it being possible for a thoracic aneurysm to occur in what is called the ascending branch of the aorta (Aorta ascendens), in the aortic arch and/or in the descending branch of the aorta.

In the case of thoraco-abdominal aortic aneurysms, the aneurysm does not just remain confined to a limited part of the principal artery but is located both in the chest cavity, that is to say the thorax, and in the abdominal cavity (abdomen).

A thoraco-abdominal aortic aneurysm is a very complex clinical picture and is difficult to treat. Before the aortic stent became established, it was almost always necessary to open both the thorax and the abdominal cavity. It is nowadays alternatively possible, in the context of hybrid operations, for opening of the abdominal cavity to be performed in combination with an aortic stent, or for total endovascular treatment of thoraco-abdominal aortic aneurysms to be performed.

In the case of thoraco-abdominal aortic aneurysms, the situation is almost always made more difficult by the fact that arteries of all the major organs (arteries of the intestines, celiac trunk, renal arteries) are affected during the repair work and have to be reconstructed in some form or another. Treatment of a thoraco-abdominal aneurysm is therefore difficult, involves complications, and is often carried out by specialist centers.

The vascular prostheses used in the treatment have to meet many requirements, in particular with regard to the size, length and morphology of the aneurysm and native aorta to be bridged. The permeability of the segmental arteries in this region, the coexistence of other aneurysms, and the diameter of the iliac and femoral vessels also play an important role.

As before, there is therefore still a great need for stent/stent graft systems, or vascular prostheses, with the aid of which the intervention described above could be made easier and reduced in time.

SUMMARY OF THE INVENTION

According to the invention, this object is achieved by a self-expanding vascular prosthesis for implantation in a blood vessel of a patient, particularly in the thoraco-abdominal aortic region, with a vascular prosthesis trunk having a hollow-cylindrical main body and also a first and a second opening, and with at least two vascular prosthesis side branches which branch off from the vascular prosthesis trunk and are formed integrally with the vascular prosthesis trunk, wherein the vascular prosthesis trunk has a first vascular prosthesis trunk longitudinal portion, which comprises the first opening, a second vascular prosthesis trunk longitudinal portion, which comprises the second opening, and at least two central vascular prosthesis trunk longitudinal portions which are arranged between the first and second vascular prosthesis trunk longitudinal portions and which are arranged one behind the other, and wherein the at least two vascular prosthesis side branches branching off from the vascular prosthesis trunk are arranged in the central vascular prosthesis trunk longitudinal portions, wherein furthermore the first and second vascular prosthesis trunk longitudinal portions each have a constant diameter along their respective longitudinal direction and are arranged concentrically with respect to each other, and wherein the diameter of the first vascular prosthesis trunk longitudinal portion is greater than the diameter of the second vascular prosthesis trunk longitudinal portion; the vascular prosthesis according to the invention is moreover characterized in that the first and second central vascular prosthesis trunk longitudinal portions each taper toward the second vascular prosthesis trunk longitudinal portion only in one part of the circumference and not over the entire respective circumference, wherein the respectively tapering circumferential parts of the first and second central vascular prosthesis trunk longitudinal portions are arranged in a manner offset in relation to each other in the circumferential direction, and in that at least one vascular prosthesis side branch in the first central vascular prosthesis trunk longitudinal portion and at least one second vascular prosthesis side branch in the second central vascular prosthesis trunk longitudinal portion are arranged in the respectively tapering circumferential part.

The object of the invention is further achieved by the use of the self-expanding vascular prosthesis according to the invention for the treatment of a thoraco-abdominal aneurysm.

The object of the invention is thereby achieved in full.

With the self-expanding vascular prosthesis according to the invention, a vascular prosthesis module is made available with which thoraco-abdominal aneurysms can be successfully bridged, while at the same time reliably ensuring the supply of blood to the branching-off side vessels, for example the visceral arteries, through the vascular prosthesis side branches. The vascular prosthesis side branches which branch off/issue from the vascular prosthesis trunk, and which are formed integrally with the vascular prosthesis trunk, extend in the distal direction and parallel to the longitudinal direction of the vascular prosthesis trunk and are releasable, together with the vascular prosthesis trunk, in the same vessel; this means that the side branches and the openings of the vascular prosthesis trunk are released or releasable in the same main vessel. According to the invention, the side branches of the vascular prosthesis according to the invention are therefore dimensioned and designed, particularly in respect of their length and integration with the vascular prosthesis trunk, such that they are releasable in the main vessel presenting the aneurysm. For example, further stents/stent grafts can be fitted via these side branches of the vascular prosthesis located in the main vessel, which stents/stent grafts are then inserted into branching-off vessels in order to ensure continued supply of blood.

By virtue of the reduced diameter in the central vascular prosthesis portion, it is ensured that the side branches extending in this region can easily expand and form good docking points for stents/stent grafts that are to be attached and branch off into side vessels. At the same time, the main vessel can be supplied with blood as before, via the second opening of the vascular prosthesis trunk, which second opening has a reduced diameter compared to the first opening.

Here, "taper only in one circumferential part, or part of the circumference, and not over the entire respective circumference" means, with respect to the first and the second central vascular prosthesis trunk longitudinal portions, that the central vascular prosthesis trunk portions do not taper toward the second, distal vascular prosthesis trunk longitudinal portion over the entire respective circumference, but instead only over or within one portion of the circumference, i.e. a part of the circumference. In this way, the vascular prosthesis according to the invention has as it were two "sides" in the central vascular prosthesis trunk portions, namely a side where the respective central vascular prosthesis portion tapers, and a side where the respective central vascular prosthesis portion does not taper.

The tapering part preferably occupies between one third and two thirds, more preferably approximately one half, of the circumference of the respective first and second central vascular prosthesis trunk longitudinal portions.

It is preferable if the tapering circumferential part of the first central vascular prosthesis longitudinal portion merges into the non-tapering circumferential part of the distally adjoining second central vascular prosthesis longitudinal portion, and if the non-tapering circumferential part of the first central vascular prosthesis longitudinal portion merges into the tapering circumferential part of the distally adjoining second central vascular prosthesis longitudinal portion.

By virtue of the structure of the vascular prosthesis according to the invention, the side branches extending in the region of the second, distal opening do not press the latter together as soon as they are expanded. A further advantage is that, upon expansion of the side branches, the vessel wall in this region is not subjected to additional pressure loads, which would occur in the case of a uniform diameter of the vascular prosthesis trunk in the region of the off-branching side branches.

Presently, "vascular prosthesis trunk" designates the main body of the cylindrical vascular prosthesis, from which main body the side branches branch off and extend in the distal direction and parallel to the axial longitudinal axis of the vascular prosthesis.

The prosthesis is formed as a whole in one piece. For this purpose, the prosthesis according to the invention has a prosthesis material onto which individual meandering stent rings are affixed, preferably sewn. The stent rings are in this case not connected directly to one another, but instead only via the integral prosthesis material. The stent rings have ogives/pointed arches pointing in the proximal and distal directions. Moreover, the one or more side branches are secured on the vascular prosthesis trunk.

In principle, in the case of vascular prostheses or endoluminal stent grafts, the respective ends are generally, and in the present case, referred to by the terms "distal" and "proximal", where the term "distal" designates that part or end lying farther downstream in relation to the blood flow. By contrast, the term "proximal" designates, again in relation to the blood flow, a part or the end lying farther upstream in relation to the blood flow. To put it another way, the term "distal" means in the direction of the blood flow, and the term "proximal" means counter to the direction of the blood flow. In the case of catheters, by contrast, or insertion systems, the term "distal" designates the end of the catheter or insertion system that is inserted into the patient, or the end farthest away from the user, and the term "proximal" designates the end nearer the user.

Presently, therefore, the second central vascular prosthesis trunk longitudinal portion is by definition arranged immediately distally, or in the distal direction, from the first central vascular prosthesis trunk longitudinal portion.

According to a preferred embodiment of the self-expanding vascular prosthesis according to the invention, at least one vascular prosthesis side branch is arranged in the first central vascular prosthesis trunk longitudinal portion and extends in the distal direction and parallel to the axial longitudinal axis of the hollow-cylindrical main body. According to a further embodiment of the self-expanding vascular prosthesis according to the invention, at least one vascular prosthesis side branch is arranged in the second central vascular prosthesis trunk longitudinal portion and extends in the distal direction and parallel to the axial longitudinal axis of the hollow-cylindrical main body. In the present text, "at least one side branch" signifies preferably one, two, three or four side branches.

According to a further embodiment of the self-expanding vascular prosthesis according to the invention, a total of four vascular prosthesis side branches are arranged in the two central vascular prosthesis trunk longitudinal portions. Preferably, and according to a further embodiment, these side branches are arranged on the vascular prosthesis trunk in such a way that two of them are located in the first central vascular prosthesis trunk longitudinal portion, over the circumference thereof, specifically in the tapering circumferential part, and the two others are arranged in the second central vascular prosthesis trunk longitudinal portion, likewise over the circumference thereof, in the tapering circumferential part of the second central vascular prosthesis trunk longitudinal portion.

In a development of the self-expanding vascular prosthesis according to the present invention, the first, proximal vascular prosthesis trunk longitudinal portion is longer than the two central vascular prosthesis trunk longitudinal portions and/or than the second, distal vascular prosthesis trunk longitudinal portion. In other words, this means that the first vascular prosthesis trunk longitudinal portion has a length which is greater than the length both of the central vascular prosthesis trunk longitudinal portion and also of the second, distal vascular prosthesis trunk longitudinal portion. In a further embodiment, the length of the first, proximal vascular prosthesis trunk longitudinal portion is longer than the lengths of the central and second, distal vascular prosthesis trunk longitudinal portions.

In a preferred embodiment, the first, proximal vascular prosthesis trunk longitudinal portion has a length of ca. 40 mm to ca. 100 mm, preferably ca. 50, 60, 70 or ca. 80 mm, the first central vascular prosthesis trunk longitudinal portion has a length of ca. 10 mm to ca. 30 mm, preferably ca. 10, 15, 25 mm, preferably ca. 8, 10, 12, 14, 16, 18 or 20 mm, and the second, distal vascular prosthesis trunk longitudinal portion has a length of ca. 10 mm to ca. 50 mm, preferably ca. 20, 30 or 40 mm. It will be clear to a person skilled in the art that the dimensions are dictated by the circumstances presented by the respective vessels that are to be treated with the prosthesis according to the invention. The total length of the vascular prosthesis according to the invention can be between 100 and 140 mm, preferably 110, 120 or 130 mm.

All of the dimensions specified in the present invention by "ca." signify not only the quite specific value given in each case, but also slight divergences upward or downward within the range of the manufacturing tolerances. For example, "ca." signifies that the dimensions can in each case deviate by ±0.5 mm from the cited value.

The diameter of the first, proximal vascular prosthesis trunk longitudinal portion can have a size of ca. 24 to 50 mm, and the diameter of the second, distal vascular prosthesis trunk longitudinal portion can have a size of ca. 10 to 30 mm. The diameter of the side branches can be between 5 and 10, preferably 6 and 9 mm, wherein the diameter of the side branches in the second central vascular prosthesis trunk longitudinal portion is generally smaller than that of the side branches in the first central vascular prosthesis trunk longitudinal portion. The following are illustrative values: the diameter of the one or more side branches of the first central vascular prosthesis trunk longitudinal portion is 8 mm, at the same time the diameter of the one or more side branches of the second central vascular prosthesis trunk longitudinal portion is 6 mm, the diameter for the first, proximal vascular prosthesis trunk longitudinal portion, and therefore also for the first opening, is ca. 36 mm, and the diameter for the second, distal vascular prosthesis trunk longitudinal portion, and therefore also for the second opening, is ca. 18 mm.

In a development of the vascular prosthesis according to the invention, two vascular prosthesis side branches are provided respectively in the first and in the second vascular prosthesis trunk longitudinal portions, wherein, with respect to the circumference of the vascular prosthesis trunk, the two vascular prosthesis side branches of the first central vascular prosthesis trunk longitudinal portion are attached and arranged in a manner offset in relation to the two vascular prosthesis side branches of the second central vascular prosthesis trunk longitudinal portion.

Herein and in the text below, "attached" means that the side branches on the respective circumference of the central vascular prosthesis trunk longitudinal portion are fixed to the vascular prosthesis trunk via one of their two ends, while the respective second end of the side branches is free.

According to a further embodiment of the self-expanding vascular prosthesis, provision is made that, with respect to a radial axis extending perpendicular to the axial longitudinal axis extending through the first and second concentrically arranged vascular prosthesis trunk longitudinal portions, the two vascular prosthesis side branches of the first central vascular prosthesis trunk longitudinal portion are arranged in the tapering circumferential part, respectively to the right and left of the axis, at an angle of in each case between ca. 30° and 60°, preferably ca. 45°.

This embodiment has the advantage that the offset distribution of the emerging side branches over the circumference of the vascular prosthesis trunk achieves as it were a uniform distribution of material in the vessel, and accumulation of material at one location of the vascular prosthesis trunk is avoided.

According to a further embodiment of the self-expanding vascular prosthesis according to the present invention, provision is made that, with respect to a radial axis extending perpendicular to the longitudinal axis extending through the first and second concentrically arranged vascular prosthesis trunk portions, the two vascular prosthesis side branches of the second central vascular prosthesis trunk longitudinal portion are attached and arranged in the tapering circumferential part, respectively to the right and left of the radial axis, at an angle of in each case between ca. 120° and 150°, preferably 135°.

With this embodiment too, an accumulation of material can be avoided.

As has been mentioned above, and according to a further embodiment of the self-expanding vascular prosthesis according to the invention, the vascular prosthesis trunk and/or the vascular prosthesis side branches have stent springs or stent rings which are arranged at a distance behind one another in the longitudinal direction and which each extend in a meandering formation, which stent spring/rings are connected to one another only or exclusively via a prosthesis material, and not directly, for example via bridges or connection points.

As has likewise been mentioned above, the vascular prosthesis according to the invention has, in a preferred embodiment, stents which are connected to one another via a biocompatible graft material or prosthesis material on the side facing toward the vessel wall. The stents are in the form of meandering stent rings which are made of a self-expanding shape-memory material, preferably Nitinol, and which have ogives or struts pointing alternately in the proximal direction and distal direction. The side branches can also be constructed in this way. A more detailed description of such stents and of the graft/prosthesis material is to be found, for example, in DE 103 37 739, the entire content of which is hereby referenced.

In the vascular prosthesis according to the invention, it is generally preferable if the prosthesis material comprises a material selected from a textile or a polymer.

In particular, it is preferable if the prosthesis material comprises a material or is formed from a material that is selected from polyester, polyurethane, polystyrene, polytetra-fluoroethylene, ultra-high-molecular-weight polyethylene (UHMPE), or mixtures thereof.

In one embodiment, the vascular prosthesis according to the invention has, in the first, proximal and in the second, distal vascular prosthesis portion, at least one stent ring, preferably two or three stent rings with ogives/pointed arches extending uniformly, i.e. with the same amplitude, in the proximal and distal directions and pointing alternately in the distal and proximal directions. According to a further embodiment, the stent ring mounted at the proximal end of the vascular prosthesis is secured to the prosthesis material only by way of its distally facing ogives/pointed arches, not its proximally facing ogives/pointed arches.

According to a further embodiment, the central vascular prosthesis trunk longitudinal portions have stent rings with different ogives/pointed arches, i.e. ogives/pointed arches extending with different amplitude in the proximal and distal directions. The tapering circumferential parts can be effected, for example, by narrower stent rings in this region. In a preferred embodiment, the first central vascular prosthesis trunk longitudinal portion has two such stent rings, and the second central vascular prosthesis trunk longitudinal portion has one such stent ring. In a preferred embodiment, the side branches can also have at least one stent ring, preferably one stent ring, with a different amplitude of the ogives/pointed arches.

In a development of the vascular prosthesis according to the invention, radiopaque markers are provided at least in the region of the ends of the vascular prosthesis trunk and/or the ends of the side branches of the vascular prosthesis, and/or in the region of emergence of the vascular prosthesis side branches from the vascular prosthesis trunk.

Preferably, the radiopaque markers are made of one or more of the following materials, for example gold, palladium, tantalum, chromium, silver, etc.; the shape of the markers may in this case be any desired form, for example round, angular, and/or for example have the form of letters, numbers or figures that are helpful for the orientation of the prosthesis in the vessel.

According to a further embodiment of the vascular prosthesis according to the invention, the vascular prosthesis side branches branching off from the vascular prosthesis trunk are connected to the vascular prosthesis trunk via oval openings in the respective tapering circumferential part of the vascular prosthesis trunk.

In a further embodiment, the vascular prosthesis trunk is designed for placement in the thoraco-abdominal aorta, and the vascular prosthesis side branches are designed to supply the visceral arteries.

According to a development of the vascular prosthesis according to the invention, it moreover comprises at least a first stent graft, with a first and a second stent graft opening, and also with a lumen extending between the stent graft openings, wherein the first stent graft opening is designed and dimensioned for partial insertion into the second opening of the vascular prosthesis.

In a further embodiment, the vascular prosthesis according to the invention moreover comprises at least a second vascular prosthesis, with a first and a second vascular prosthesis opening, and also with a lumen extending between the vascular prosthesis openings, wherein the first vascular prosthesis opening is designed for partial insertion into the vascular prosthesis side branches, in order to supply the side vessels branching off from a main vessel.

In this embodiment, it is preferable if the second vascular prosthesis is stented or unstented.

Further advantages will become clear from the figures and from the following description of preferred illustrative embodiments.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are explained in more detail in the following description and shown in the drawing, in which.

DESCRIPTION OF PREFERRED EMBODIMENTS

Figure 1:
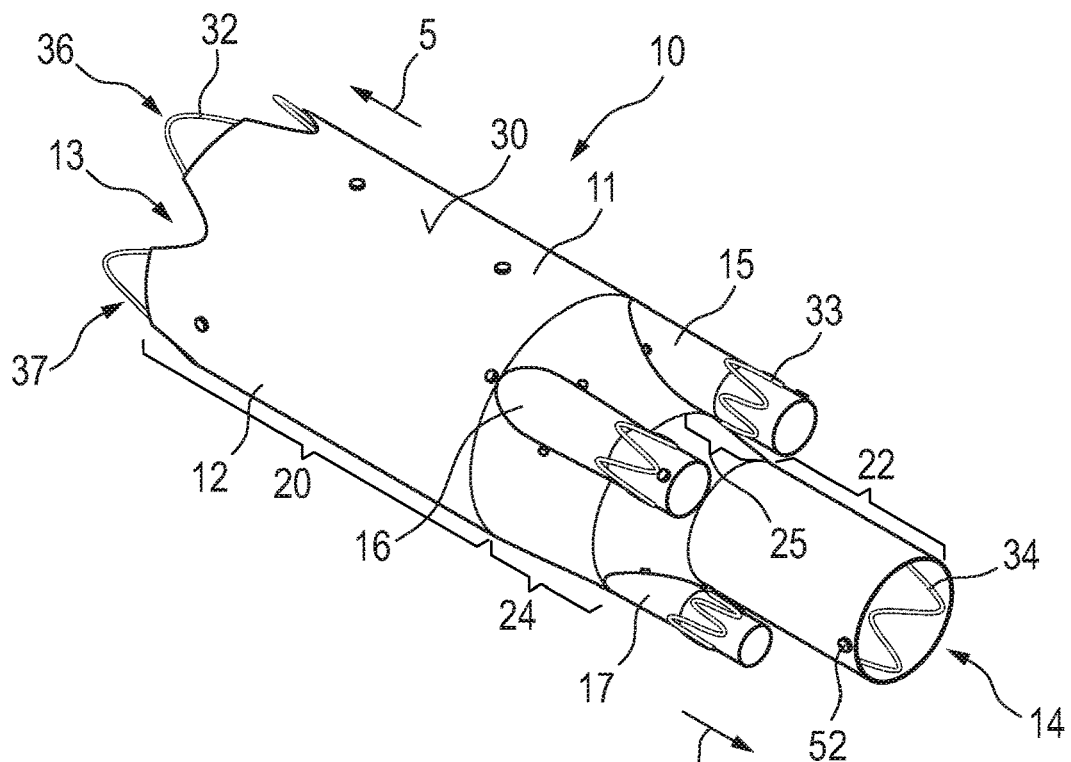
FIG. 1 shows a schematic view of an embodiment of a vascular prosthesis according to the invention in the non-inserted, expanded state, specifically a perspective view of the long side from above.

In the figures, identical features are provided with identical reference signs. For the sake of clarity, the figures do not always show all of the reference signs.

In FIGS. 1 to 4, reference sign 10 designates the whole of a vascular prosthesis, having a generally hollow-cylindrical main body 11 and having a vascular prosthesis trunk 12 with a first, proximal opening 13 and a second, distal opening 14. The vascular prosthesis 10 moreover has side branches 15, 16, 17, 18 branching off/issuing from the vascular prosthesis trunk 12. On account of the view being a perspective view, the side branch 18 is not shown in FIG. 1, and the side branch 17 is not shown in FIG. 2.

Figure 2:
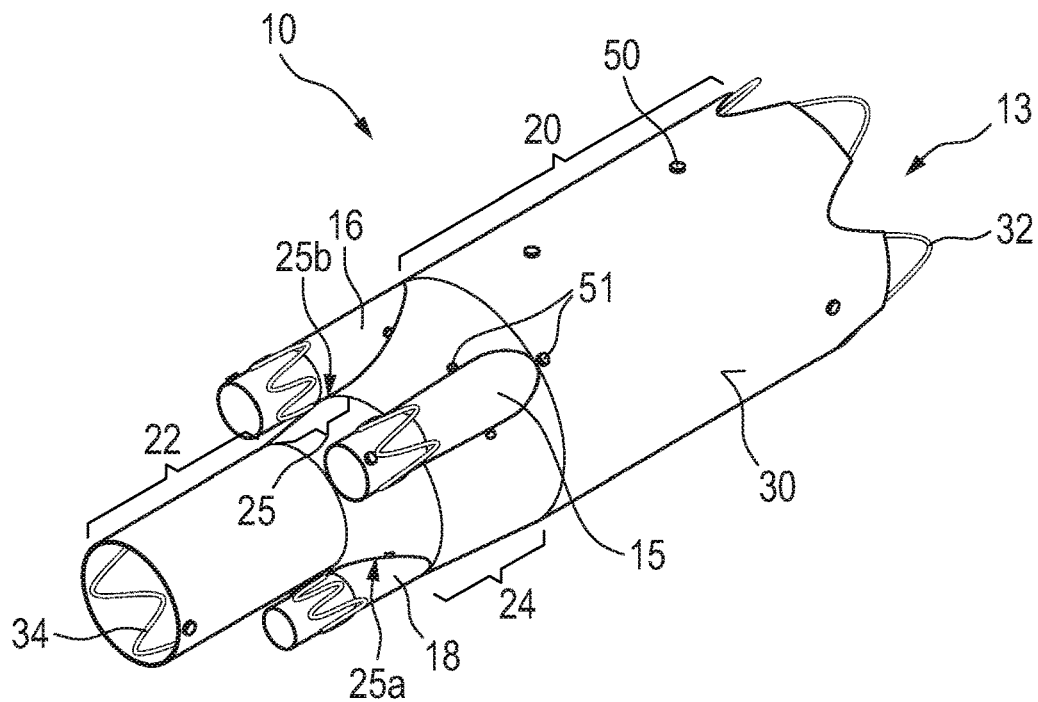
FIG. 2 shows the embodiment from FIG. 1 from the other side.

The vascular prosthesis shown in FIGS. 1 and 2 moreover has an first, proximal vascular prosthesis trunk longitudinal portion 20, which comprises the first opening 13, and a second, distal vascular prosthesis trunk longitudinal portion 22, which comprises the second opening 14. FIGS. 1 and 2 also show that the vascular prosthesis 10 additionally has two central vascular prosthesis trunk longitudinal portions 24 and 25, which are arranged one behind the other between the first and second vascular prosthesis trunk longitudinal portions 20, 22.

The two side branches 15 and 16 extend from the first central vascular prosthesis trunk longitudinal portion 24, while the two side branches 17, 18 extend from the second central vascular prosthesis trunk longitudinal portion 25, in each case in the distal direction as indicated by the arrow 6.

Figure 5:
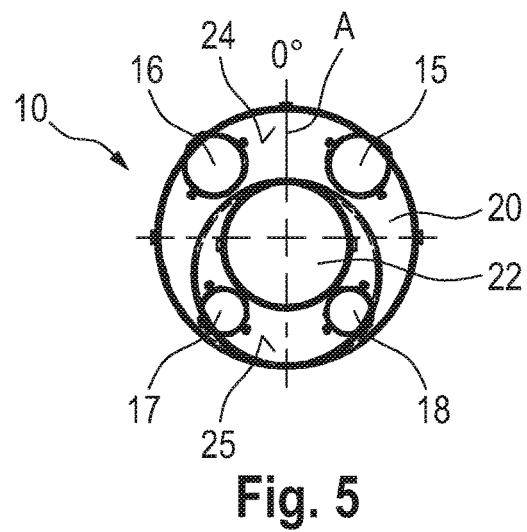
FIG. 5 shows a schematic view of the embodiment shown in FIGS. 1 to 4, specifically a frontal view through the distal end to the proximal end.

The first, proximal vascular prosthesis trunk longitudinal portion 20 and the second, distal vascular prosthesis trunk longitudinal portion 22 each have substantially constant diameters d1 and d2 along their length and are arranged concentrically with respect to each other (see also FIG. 5 in this connection). The diameter d1 of the first, proximal vascular prosthesis trunk longitudinal portion 20 is greater than the diameter d2 of the second, distal vascular prosthesis trunk longitudinal portion 22.

The vascular prosthesis 10 shown in FIGS. 1 to 4 moreover has a prosthesis material 30 which extends along the entire length L of the vascular prosthesis 10 and on which stent rings 32, 33, 34 and 35 are mounted. The stent rings 32, 33, 34 and 35 constitute ogives/pointed arches 36 which extend in a meandering formation, are formed from one wire and alternately point in the proximal direction 5 and distal direction 6, which ogives/pointed arches 36 are connected to one another by struts 37. For the sake of clarity, FIGS. 1 and 2 show only the stent rings 32 and 34 surrounding the respective openings 13 and 14, and also the stent rings 33 of the side branches.

The stent ring 32 is located at the proximal end of the vascular prosthesis 10 and is applied, preferably sutured, circumferentially about the opening 13 onto the prosthesis material 30 from the direction of the inner face of the hollow-cylindrical main body 11. As can be seen in particular from FIGS. 3 and 4 described below, the stent ring 32 has ogives/pointed arches 36 of the same amplitude, i.e. the struts 37 connecting the ogives/pointed arches 36 are all of the same length. FIGS. 1 and 2 show that the stent ring 32 is applied to the prosthesis material 30 only over the ogives/pointed arches 36 pointing in the distal direction 6, and also over a portion of the struts 37 connecting these, such that the ogives/pointed arches 36 pointing in the proximal direction 5 are free of prosthesis material.

In the embodiment shown in FIGS. 1 to 4, the stent rings 33 of the side branches 15, 16, 17 and 18 are fixed, preferably sutured, onto the prosthesis material 30 from the outside. These stent rings 33 have different amplitudes, i.e. the supports 37 connecting the ogive/pointed arches s 36 are of different lengths here.

The stent ring 34 is provided at the distal end in the second, distal vascular prosthesis trunk longitudinal portion 22 and is applied, preferably sutured, onto the prosthesis material 30 circumferentially about the opening 14, from the direction of the inner face of the hollow-cylindrical main body 11. As can be seen in particular from FIGS. 3 and 4 described below, the stent ring 34 has ogives/pointed arches 36 of the same amplitude, i.e. the supports 37 connecting the ogives/pointed arches 36 are all of the same length. The stent ring 34 is fixed on the prosthesis material 30 across the entire surface defined by it.

Figure 3:
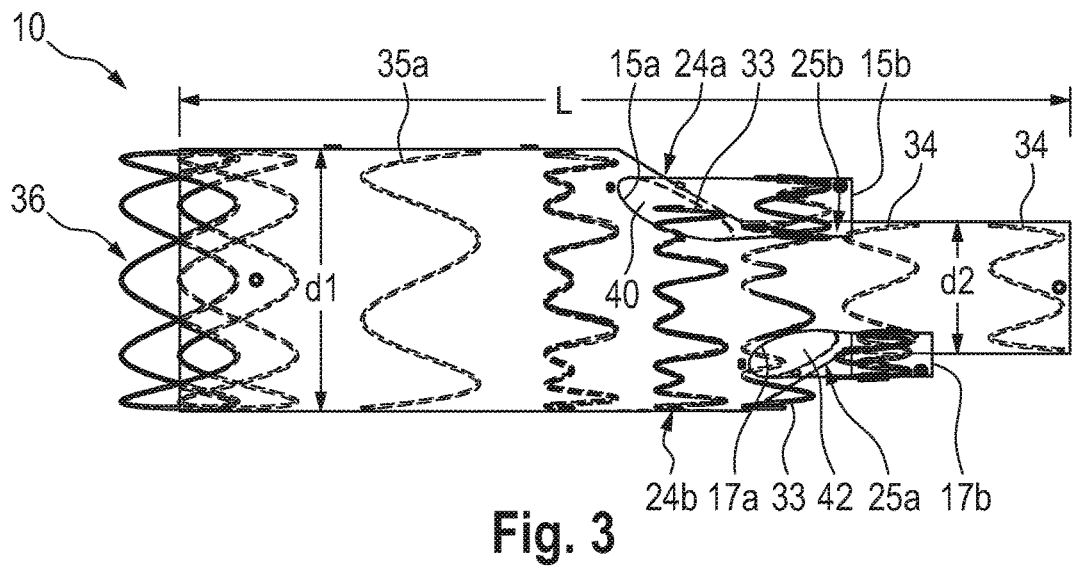
FIG. 3 shows another schematic view of the embodiment from FIG. 1, specifically a full lateral view of the long side, with the stent rings plotted schematically.
Figure 4:
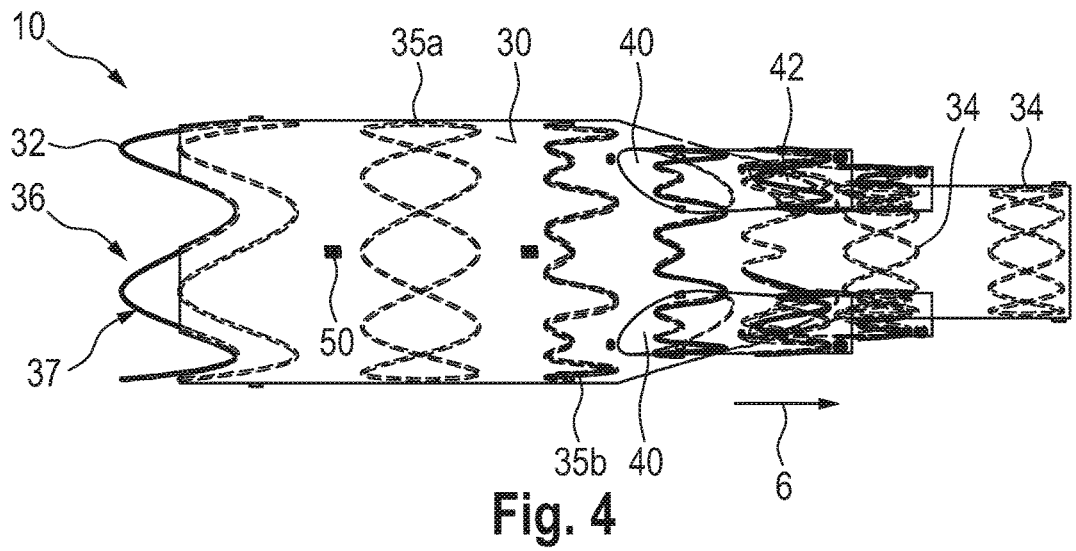
FIG. 4 shows the same schematic view as in FIG. 3, in a longitudinal view from above.

The first, proximal vascular prosthesis trunk longitudinal portion 20 and also the second, distal vascular prosthesis trunk longitudinal portion 22 can each have further stent rings 32, 33, 34 or 35 which are arranged at a certain distance one behind the other along the respective length of the vascular prosthesis trunk longitudinal portion 20, 22 in question, as can be seen in particular from FIGS. 3 and 4. Here, reference sign 35a designates a further stent ring which is downstream from the stent ring 32 in the first, proximal vascular prosthesis trunk longitudinal portion 20 and is likewise fixed from the inside onto the prosthesis material 30. This stent ring 35a also has a uniform amplitude. The second, distal vascular prosthesis trunk longitudinal portion 22 also has a second stent ring 34 with a uniform amplitude. The first, proximal vascular prosthesis trunk longitudinal portion 20 moreover has a stent ring 35b with an irregular amplitude, i.e. the struts connecting the ogives/pointed arches 36 in this case have different lengths.

It will also be seen from FIGS. 3 and 4 that the first central vascular prosthesis trunk longitudinal portion 24 and the second central vascular prosthesis trunk longitudinal portion 25 each have a stent ring 33, and these stent rings 33 each have nonuniform amplitudes.

FIGS. 1 to 4 also show that the first and second central vascular prosthesis trunk longitudinal portions 24, 25 each taper in the distal direction in one of their circumferential parts 24a, 24b, as it were "unilaterally". This can be seen in particular from the side view in FIG. 3. Here, the first central vascular prosthesis trunk longitudinal portion 24 has, at its circumference, a circumferential part 24a which, in side view, tapers obliquely in the distal direction 6, whereas the circumferential part 24b does not taper and, in side view, therefore extends in a straight line. In the plan view shown in FIG. 4, it can be seen that the tapering circumferential part 24a of the first central vascular prosthesis trunk longitudinal portion 24 occupies ca. half of the circumference of the central vascular prosthesis trunk longitudinal portion 24. In this tapering circumferential part 24a, oval openings 40 are located in the prosthesis material 30 of the vascular prosthesis 10. At their end 15a connected to the vascular prosthesis trunk, the side branches 15 and 16 are fitted over these oval openings 40, while the end 15b extends freely in the distal direction 6.

It will be seen from FIGS. 1 and 2 that the second central vascular prosthesis trunk longitudinal portion 25 also has, at its circumference, a circumferential part 25a which, in side view, tapers obliquely in the distal direction 6, whereas the circumferential part 25b does not taper and, in side view, therefore extends in a straight line. In the side views in FIGS. 1 and 2, it can be seen that the tapering circumferential part 25a of the second central vascular prosthesis trunk longitudinal portion 25 occupies ca. half of the circumference of the second central vascular prosthesis trunk longitudinal portion 25. Also in this tapering circumferential part 25a, oval openings 42 (see FIGS. 3 and 4) are located in the prosthesis material 30 of the vascular prosthesis 10. At their end 17a connected to the vascular prosthesis trunk 12, the side branches 17 and 18 are fitted over these oval openings 42, while the end 17b extends freely in the distal direction 6.

It will also be seen, in particular from FIGS. 3 and 4, that the tapering circumferential part 24a of the vascular prosthesis trunk longitudinal portion 24 directly adjoins the non-tapering circumferential part 25b of the second vascular prosthesis trunk longitudinal portion 25 in the distal direction 6. On the other side, the non-tapering circumferential part 24b of the first central vascular prosthesis trunk longitudinal portion 24 merges into the tapering circumferential part 25a of the second central vascular prosthesis trunk longitudinal portion 25.

In FIGS. 1 to 4, radiopaque markers 50, 51, 52 are also provided, wherein the markers 50, in the illustrative embodiment shown in FIGS. 1 to 4, are arranged centrally on the prosthesis material 30 at a defined distance from each other and parallel to the longitudinal axis of the vascular prosthesis 10. The markers 51 are arranged around the oval openings 40, 42, in order to mark the emerging side branches 15, 16, 17 and 18. The marker 52 is mounted in the region of or at the second, distal opening 14, in order to suitably indicate the latter to the operating surgeon in the X-ray control.

FIG. 5, finally, shows the plan view into the lumen of the hollow-cylindrical main body 11, specifically looking into the second, distal opening 14 in the direction of the first, proximal opening 13. It will be seen here that the first and second vascular prosthesis trunk longitudinal portions 20, 22 have different diameters d1 and d2 and, in addition, are arranged concentrically to each other.

It will also be seen from this figure that, with respect to an axis A extending perpendicular to the longitudinal axis L extending through the first and second concentrically arranged vascular prosthesis trunk longitudinal portions 20, 22, the side branches 15 and 16 are arranged in the tapering circumferential part 24b, respectively to the right and left of the axis A, at an angle of ca. 45°.

On the other hand, with respect to the axis A, the side branches 17 and 18 are arranged in the tapering circumferential part 25b, respectively to the right and left of the axis A, at an angle of ca. 135°.

The advantageous features of the central vascular prosthesis trunk longitudinal portions 24, 25 thus result in the possibility of arranging the side branches in a way that saves material and space.

What is claimed is:

1. A self-expanding vascular prosthesis for implantation in a blood vessel of a patient, with
   a vascular prosthesis trunk having a hollow-cylindrical main body and also a first and a second opening, and with at least two vascular prosthesis side branches which branch off from the vascular prosthesis trunk and are formed integrally with the vascular prosthesis trunk, wherein the vascular prosthesis trunk has
   a first, proximal vascular prosthesis trunk longitudinal portion, which comprises the first opening,
   a second, distal vascular prosthesis trunk longitudinal portion, which comprises the second opening, and
   at least two central vascular prosthesis trunk longitudinal portions, which are arranged between the first and second vascular prosthesis trunk longitudinal portions and which are arranged one behind the other, and wherein the at least two vascular prosthesis side branches branching off from the vascular prosthesis trunk are arranged in the central vascular prosthesis trunk longitudinal portions,
   wherein the first and second vascular prosthesis trunk longitudinal portions each have a constant diameter d1, d2 along their respective longitudinal direction and are arranged concentrically with respect to each other, and wherein the diameter d1 of the first vascular prosthesis trunk longitudinal portion is greater than the diameter d2 of the second vascular prosthesis trunk longitudinal portion,
   wherein the first and second central vascular prosthesis trunk longitudinal portions each taper toward the second vascular prosthesis trunk longitudinal portion only in one circumferential part,
      wherein the respectively tapering circumferential parts of the first and second central vascular prosthesis trunk longitudinal portions are arranged in a manner offset in relation to each other in the circumferential direction, and
      wherein at least one vascular prosthesis side branch in the first central vascular prosthesis trunk longitudinal portion and at least one second vascular prosthesis side branch in the second central vascular prosthesis trunk longitudinal portion are arrange the respectively tapering circumferential part.

2. The self-expanding vascular prosthesis as claimed in claim 1, wherein at least one vascular prosthesis side branch is arranged in the first central vascular prosthesis trunk longitudinal portion and extends in the distal direction and parallel to ti longitudinal axis of the hollow-cylindrical main body.

3. The self-expanding vascular prosthesis (10) as claimed in claim 2, wherein, with respect to an axis (A) extending perpendicular to the longitudinal axis (L) extending through the first and second concentrically arranged vascular prosthesis trunk portions, the two vascular prosthesis side branches of the first central vascular prosthesis trunk longitudinal portion are arranged in the tapering circumferential part, respectively to the right and left of the axis (A), at an angle of in each case between ca. 30° and 60°, preferably ca. 45°.

4. The self-expanding vascular prosthesis as claimed in claim 1, wherein at least one vascular prosthesis side branch is arranged in the second central vascular prosthesis trunk longitudinal portion and extends in the distal direction and parallel to the longitudinal axis of the hollow-cylindrical main body.

5. The self-expanding vascular prosthesis as claimed in claim 4, wherein, with respect to an axis (A) extending perpendicular to the longitudinal axis (L) extending through the first and second concentrically arranged vascular prosthesis trunk portions, the two vascular prosthesis side branches of the second central vascular prosthesis trunk longitudinal portion are arranged in the tapering circumferential part, respectively to the right and left of the axis (A), at an angle of in each case between ca. 120° and 150°, preferably ca.135°.

6. The self-expanding vascular prosthesis as claimed in, claim 1, wherein a total of four vascular prosthesis side branches are arranged in the two central vascular prosthesis trunk longitudinal portions.

7. The self-expanding vascular prosthesis as claimed in claim 1, wherein the first vascular prosthesis trunk longitudinal portion is longer than the two central vascular prosthesis trunk longitudinal portions and/or than the second vascular prosthesis trunk longitudinal portion.

8. The self-expanding vascular prosthesis as claimed in claim 1, wherein two vascular prosthesis side branches are provided respectively in the first and in the second vascular prosthesis trunk longitudinal portions, wherein, with respect to the circumference of the vascular prosthesis trunk, the two vascular prosthesis side branches of the first central vascular prosthesis trunk longitudinal portion are arranged in a manner offset in relation to the two vascular prosthesis side branches of the second central vascular prosthesis trunk longitudinal portion.

9. The self-expanding vascular prosthesis (10) as claimed in claim 1, wherein the vascular prosthesis trunk and/or the vascular prosthesis side branches have stent rings Which are arranged at a distance behind One another in the longitudinal direction and each extend in a meandering formation, which stent rings are connected to one another only via a prosthesis material.

10. The self-expanding vascular prosthesis as claimed in claim 1, wherein radiopaque markers are provided at least in the region of the openings and/or of the free ends of the vascular prosthesis side branches, and/or in the region of emergence of the vascular prosthesis side branches from the vascular prosthesis trunk.

11. The self-expanding vascular prosthesis as claimed in claim 1, wherein the vascular prosthesis side branches branching off from the vascular prosthesis trunk are connected to the vascular prosthesis trunk via oval openings in the tapering circumferential part of the first and/or second vascular prosthesis trunk longitudinal portion.

12. The self-expanding vascular prosthesis as claimed in claim 1, wherein the vascular prosthesis trunk is designed for placement in the thoraco-abdominal aorta, and the vascular prosthesis side branches are designed to supply the visceral arteries.

13. The self-expanding vascular prosthesis as claimed in claim 1, wherein it moreover comprises at least a first stent graft, with a first and a second stem graft opening, and also with a lumen extending between the stem graft openings, wherein the first stent graft opening is designed and dimensioned for partial insertion into the second opening of the vascular prosthesis.

14. The self-expanding vascular prosthesis as, claimed in claim 1, wherein it moreover comprises at least a second vascular prosthesis, with a first and a second vascular prosthesis opening, and also with a lumen extending between the vascular prosthesis openings, wherein the first vascular prosthesis opening is designed for partial insertion into the vascular prosthesis side branches, in order to supply the side vessels branching off from a main vessel.

15. The self-expanding vascular prosthesis as claimed in claim 1, wherein the second vascular prosthesis is stented or unstented.

16. Method for treating a thoraco-abdominal aneurysm in a patient in need thereof, which method comprises the step of deploying the vascular prosthesis as claimed in claim 1.

* * * * *